(12) United States Patent
Narasimhamoorthy et al.

(10) Patent No.: US 10,130,066 B2
(45) Date of Patent: Nov. 20, 2018

(54) **POTATO PLANT *SOLANUM TUBEROSUM* L. DENOMINATED KI969**

(71) Applicant: Kemin Industries, Inc., Des Moines, IA (US)

(72) Inventors: Brindha Narasimhamoorthy, West Des Moines, IA (US); Liuqing Zhao, Zhuhai (CN); Xin Liu, Zhuhai (CN); John A. Greaves, Ankeny, IA (US)

(73) Assignee: KEMIN INDUSTRIES, INC., Des Moines, IA (US)

( * ) Notice: Subject to any disclaimer, the term of this patent is extended or adjusted under 35 U.S.C. 154(b) by 0 days.

(21) Appl. No.: 15/373,069

(22) Filed: Dec. 8, 2016

(65) Prior Publication Data
US 2018/0160642 A1    Jun. 14, 2018

(51) Int. Cl.
*A01H 5/06* (2018.01)
*A01H 6/82* (2018.01)
*A01H 5/04* (2018.01)

(52) U.S. Cl.
CPC ............... *A01H 6/827* (2018.05); *A01H 5/04* (2013.01)

(58) Field of Classification Search
None
See application file for complete search history.

(56) References Cited

U.S. PATENT DOCUMENTS

| | | | |
|---|---|---|---|
| 5,434,342 A * | 7/1995 | Cipar | A01H 5/04 435/417 |
| 9,750,768 B2 * | 9/2017 | Kim | C12N 5/0623 |
| 9,808,955 B2 * | 11/2017 | Murray | B27K 3/46 |
| 9,920,486 B2 * | 3/2018 | Chinn | D21H 27/20 |
| 9,932,604 B1 * | 4/2018 | Nordick | A01G 22/00 |
| 2008/0184396 A1 | 7/2008 | Hannapel et al. | |
| 2014/0115736 A1 | 4/2014 | Lindhout et al. | |
| 2014/0328994 A1 | 11/2014 | Clark et al. | |

OTHER PUBLICATIONS

International Searching Authority, "Search Report and Written Opinion," issued in connection with International Patent Application No. PCT/US2017/064909, dated Mar. 6, 2018, 10 pages.
Komarnytsky et al., "Potato protease inhibitors inhibit food intake and increase circulating cholecystokinin levels by a trypsin-dependent mechanism," Intl. Journal Obsentrics, 2011, vol. 35 (2), pp. 236-243.
Habib et al., "Plant protease inhibitors: a defense strategy in plants," Biotechnology and Molecular Biology Review vol. 2 (3), www.academicjournals.org/BMBR, pp. 068-085, Aug. 2007.
Holm, "The Colorado Potato Breeding and Selection Program—A Photo Essay," Colorado State University, 2013, Retrieved from: http://potatoes.colostate.edu/wp-content/uploads/pef/potato_breeding_photo_essay.pdf, pp. 1-8.
Ewing et al., "Shoot, Stolon, and Tuber Formation on Potato (*Solanum tuberosum* L.) Cuttings in Response to Photoperiod," Journal of Plant Physiology, vol. 61, pp. 348-353, 1978.

* cited by examiner

*Primary Examiner* — Cathy Kingdon Worley
(74) *Attorney, Agent, or Firm* — Nyemaster Goode P.C.

(57) ABSTRACT

A new and distinct clonal line plant of *Solanum tuberosum* L. named KI969 and characterized by elevated levels of proteinase inhibitor II.

15 Claims, 5 Drawing Sheets

POTATO PLANT *SOLANUM TUBEROSUM* L. DENOMINATED KI969

FIELD OF THE INVENTION

The present invention relates generally to a potato plant and, more specifically, to a plant of potato clonal line KI969 that produces a high amount of protease inhibitor II.

BACKGROUND OF THE INVENTION

Potato contains a group of inhibiting proteins that are a major part of total storage protein (Ryan et al., 1976). Proteinase inhibitor II (PI2) was originally identified and isolated from white potatoes (Bryant et al., 1976). The protein, (PI2), is one of the main ingredients in the satiety enhancement supplement, Slendesta® (Kemin Industries, Inc., Des Moines, Iowa) and is derived from the commercially available white potato variety Russet Nugget. A high PI2 accumulating potato variety is required as a sustainable biomass source for PI2 production.

SUMMARY OF THE INVENTION

The invention consists of a plant of *Solanum tubersoum* L. named KI969 that has elevated protease inhibitor II levels, excellent vigor and overall agronomic robustness. KI969 is a white skin and white flesh cultivar that was developed from a potato breeding program.

DETAILED DESCRIPTION OF PREFERRED EMBODIMENTS

A large number of germplasm collections (147 accessions and 38 cultivated varieties) of *S. tuberosum* representing worldwide variation held in the US Potato Genebank (US-PGB) were screened for PI2 variation. Plants from each accession/variety were grown to full maturity under greenhouse and field conditions alongside Russet Nugget during the summer of Year 1. Tuber samples from each plant were collected at the time of maturity and freeze dried for PI2 analysis. Dry tuber samples from each line were quantitated for PI2 content and expressed on a dry matter basis.

Figure 1:
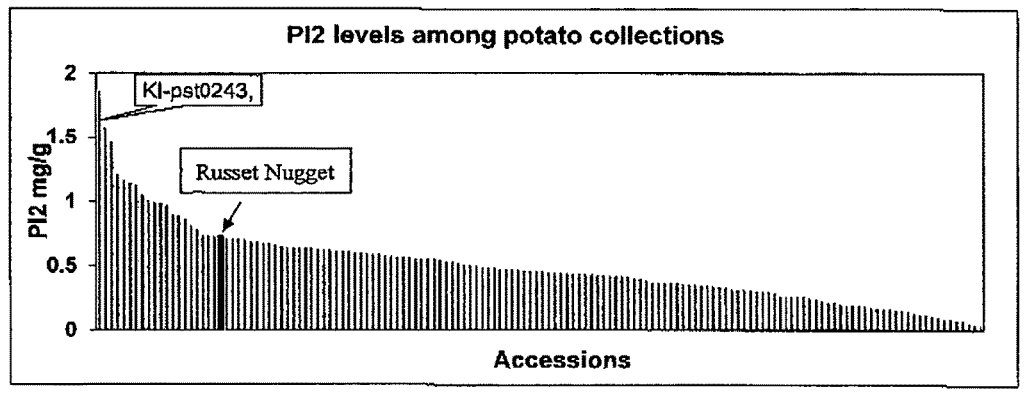
FIG. 1 is a graph showing variation among potato collections for PI2 content on a dry matter basis.

An exotic *S. tubersoum* collection from USPGB, designated as KI-PSt0243, showed the highest PI2, with almost a 2× increase in PI2 relative to Russet Nugget (FIG.1).

Figure 2:
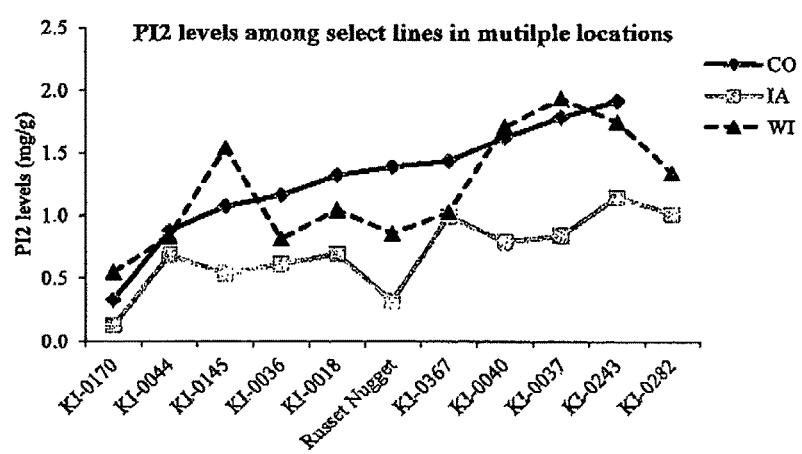
FIG. 2 is a graph showing the PI2 content among select accessions in Iowa, Wis. and Colo.

In the following year, twelve genotypes/accessions including KI-PSt0243 and Russet Nugget were evaluated in field sites in Iowa, Wis. and Colo. during May-Sep. All the genotypes/accessions were planted in a randomized replicated trial in all three locations along with Russet Nugget as control. Tubers from ten accessions that grew up to maturity were harvested and freeze-dried for PI2 quantitation. PI2 levels were generally lower at the Iowa location. The high and the low PI2 accessions generally remained the same for PI2 ranking at all locations, with slight differences in ranks between locations (FIG.2). In this study, KI-PSt0243 was found to be have higher PI2 in all three locations (FIG.2). KI-PSt0243 was further utilized in the breeding program for developing high PI2 cultivars.

Figure 3:
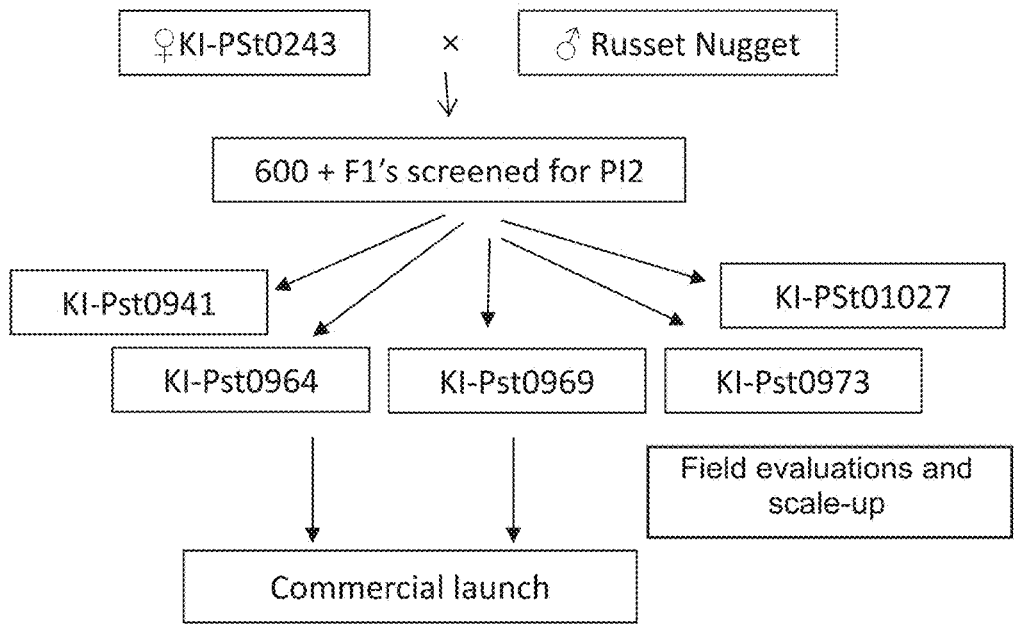
FIG. 3 is a schematic diagram of the breeding scheme for development of KI969.

Simultaneously, KI-PSt0243 was crossed to Russet Nugget as shown in FIG. 3. Seed from the cross were planted to generate over 600 F1 plants. Each plant was grown under greenhouse conditions for producing tubers. Tubers of all the F1 plants that grew up to maturity were harvested and freeze-dried for PI2 quantitation. Fifty F1 progeny from the cross KI-PSt0243 x Russet Nugget with PI2 levels higher than Russet Nugget were chosen.

Tubers from these selections were multiplied in a greenhouse during January to April, Year 3 . To enable sprouting, the tubers were treated with ProGibb® (Velent BioSciences Corporation), planted in germination soilless mix and placed on heating pads. After 4 weeks, plantlets were transferred to 5 gallon pots. When the plantlets were approximately one month old, leaf tissue from each plant was tested for the presence of viruses at the potato certification lab of Colorado State University (CSU). All of the selections tested negative and tubers from each of the selections were bulked until the 1st week of April. From among 50 F1 lines planted, only 38 of them yielded adequate amounts of tubers for field trial purposes. Harvested tubers (seed-tubers) were treated with ProGibb® to induce sprouting and were then stored appropriately until planting. In addition, tubers from 11 accessions from the germplasm collections of the US Potato Genebank (USPGB) were included in the field trial.

Tubers from the 49 selected entries (breeding lines +US-PGB accessions) were planted at two locations; field sites at USPGB, Sturgeon Bay, Wis.; and at the CSU San Luis Valley research station, Colo. At the Wis. location, each entry was planted in short rows comprising of three to five clones per entry. All the entries were planted in two replicates in a random order. At the CSU field location each clonal line was planted in a longer row comprising of 5-10 clones per entry. Russet Nugget and KI-PSt0243 were also included in the trial for comparison with all of the other selected lines. Seed-tubers of KI-PSt0243 with similar physiological maturity as that of the seed-tubers of F1 lines were planted as a control at the Colo. location. In addition, fully mature tubers of KI-PSt0243 and Russet Nugget were also planted in adjacent fields which were used for comparison. The field trials at both locations were planted during the 3rd week of May, Year 3. The crop was grown and managed using the recommended nutrient and water management regimes specific for that location. Notes on field emergence and vigor were taken during the middle of July at each location. Plant emergence for each entry was scored as good (>70% emerged), average (40-70% emerged), poor (<40% emerged) and none, eight weeks after planting. Tubers were harvested from the Colo. field location on September 7th, Year 3; and during the last week of September at the Wis. location. A few entries from both locations did not emerge and a few that emerged did not yield tubers. Harvested tubers from other entries were scored visually into the following categories based on tuber diameter/size; "small" tubers with 1-1.5" diameter; "medium" tubers with 2-2.5" diameter; "large tubers" with 3-3.5" diameter; and "big" tubers with >4" diameter. A representative sample of the harvested tubers for each clonal line was freeze dried and quantitated for PI2 analysis. In addition, PI2 content of select individuals was quantitated by means of the radial immune-diffusion (RID) assay in agar gels containing specific antibodies.

Figure 4:
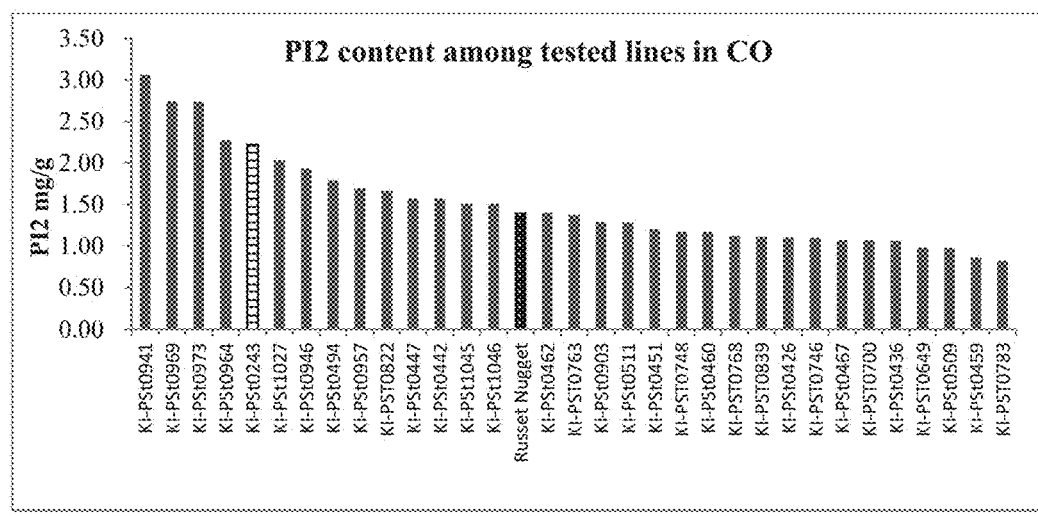
FIG. 4 is a graph of PI2 levels of selected lines under Colo. conditions in Year 3.
Figure 5:
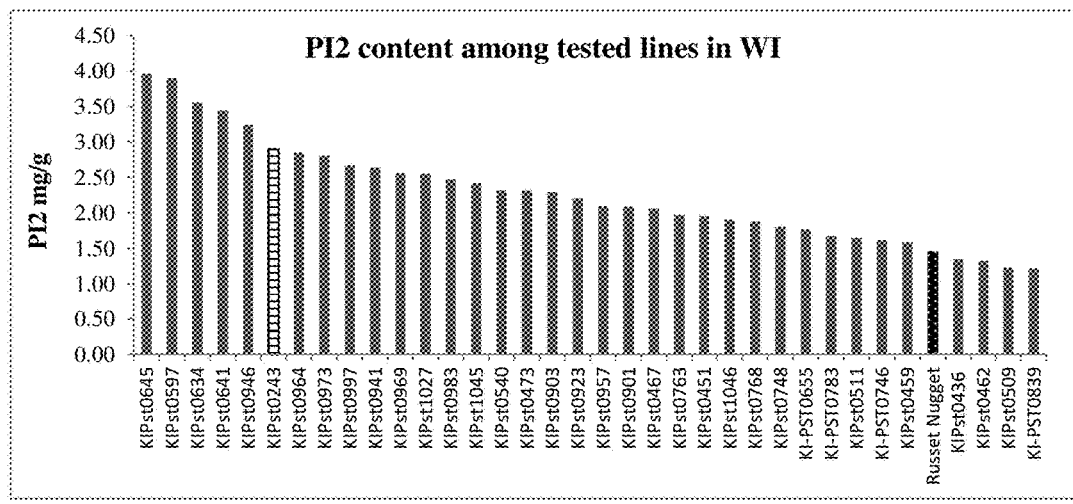
FIG. 5 is a graph of PI2 levels of selected lines under Wis. conditions in Year 3.

Five promising clonal lines KI-PSt0941, KI-PSt0969, KI-PSt0973, KI-PSt0964 and KI-PSt1027 with PI2 levels 50% or higher than Russet Nugget combined tuber size equivalent to Russet Nugget were identified from both Colo. and Wis. location (FIGS. 4 and 5). A 78% correlation between two locations for PI2 content among lines tested was observed.

The radial immune-diffusion (RID) assay reconfirmed the PI2 content of the top five lines in comparison to Russet Nugget and KI-PSt0243 as shown in Table 1.

TABLE 1

PI2 of selected potato lines quantitated by HPLC and radial immune-diffusion assay

| Sample | PI2 content (mg/g) | |
|---|---|---|
| | RID assay | HPLC assay |
| KI-PSt0941 | 2.80 | 3.06 |
| KI-PSt0969 | 2.30 | 2.75 |
| KI-PSt0973 | 2.50 | 2.73 |
| KI-PSt0964 | 2.50 | 2.22 |
| KI-PSt1027 | 2.40 | 2.03 |
| Russet Nugget | 1.40 | 1.40 |
| KI-PSt0243 | 1.70 | 1.74 |

Figure 6:
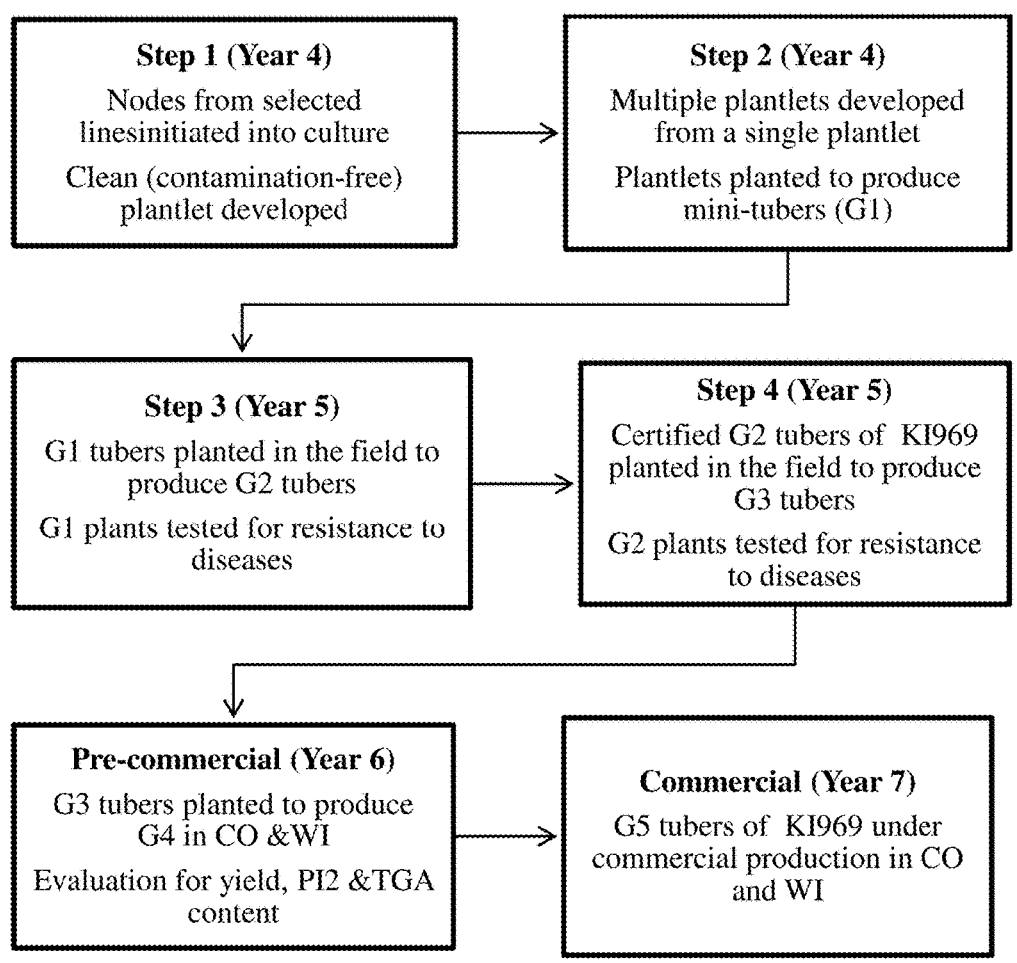
FIG. 6 is a schematic diagram of the scale-up process of KI969.

Based on the above evaluations, five line K1941, K1964, K1969, K1273 and K11027 were nominated as pre-commercial lines and entered into a state certified seed production system in Colo. in January, Year 4. Potato, being a vegetatively propagated crop, faces unique problems in maintaining varietal purity and in the management of "seed-borne" diseases. Actively growing nodes from each of these lines were placed into tissue culture to encourage disease free rapid multiplication process. Tissue cultured plants were grown to produce the next generation tubers (up to five subsequent generations) under a state controlled traditional seed production system in Colo. (FIG. 6). K1969 was chosen for its disease resistance combined with higher PI2 yield /acre compared to Russet Nugget.

K1969 plants were monitored for PI2 levels during the subsequent years while they were being scaled-up under the Colo. state certified seed production system. A 50% increase in PI2 level relative to Russet Nugget was observed throughout the evaluation period (Table 2).

TABLE 2

Average PI2 content of KI969 and Russet Nugget from multi-year evaluations

| | Year 3 | | Year 4 | | Year 5 | | Year 6 | |
|---|---|---|---|---|---|---|---|---|
| Clonal Lines | CO | WI | CO | WI | CO | WI | CO | WI |
| K1969 | 2.73 | 2.56 | 3.45 | 2.51 | 3.85 | 3.15 | 3.9 | 3.28 |
| Russet Nugget | 1.39 | 1.34 | 1.9 | 1.4 | 2.37 | 1.8 | 2.0 | 2.02 |

Figure 7:
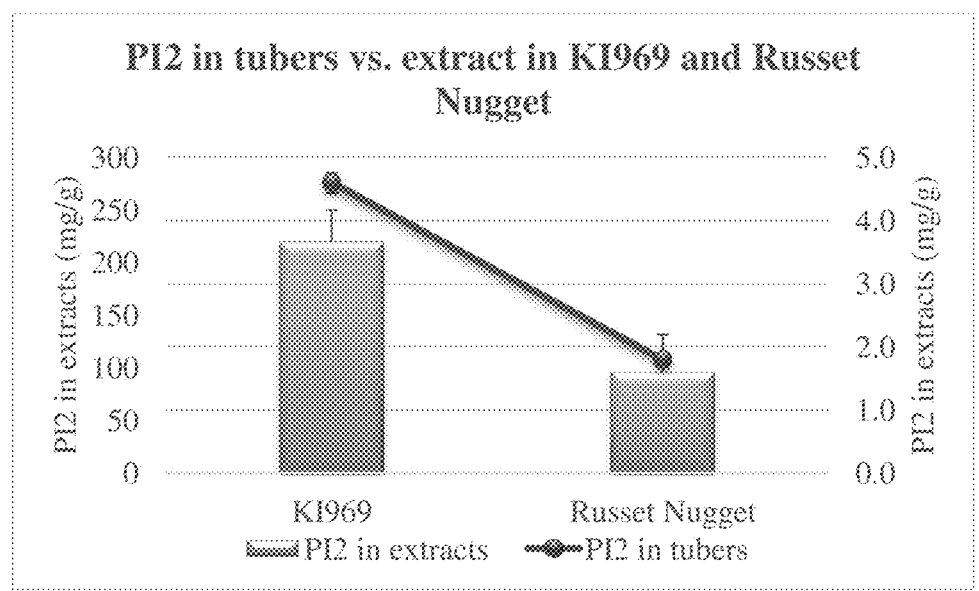
FIG. 7 is a graph of the PI2 content in tubers and final extracts of KI969 in comparison to Russet Nugget.

During Year 6, KI969 tubers were extracted and fractionated in triplicate runs through a pilot-scale PI2 extraction process in comparison to Russet Nugget using a 100 kilo volume of tubers from each of these lines. The objective was to correlate the PI2 and total glycoalkaloids (TGA) in the starting material (tubers) through to the final extract; and verify the proportional increase in PI2 and changes in TGA in the final extracts in comparison to Russet Nugget. A 50% increase was observed in PI2 content in the tubers and extracts of KI969 relative to Russet Nugget (FIG. 7).

KI969 was grown in three acres in Wis. during May to September, Year 6. PI2 from these KI969 and Russet Nugget was extracted and fractionated. PI2 in KI969 showed >50% increase over Russet Nugget. TGA in final standardized extracts were comparable to Russet Nugget. Tuber yield of KI969 was comparable to Russet Nugget.

TABLE 3

PI2 and TGA of KI969 and tuber yield relative to Russet Nugget

| Line | Tuber yield/acre | PI2 in dried tubers | PI2% in Slendesta ® extracts | TGA on 5.5% Slendesta ® extracts |
|---|---|---|---|---|
| KI969 | 40000 lbs | 3.97 mg/g | 25.02 ± 0.99 | 70 ppm |
| Russet Nugget | 40000 lbs | 2.12 mg/g | ~12 to 16 | <500 ppm |

Table 4 sets out the genotypic characteristics of KI969.

TABLE 4

Phenotypic characteristics of KI969

| | Average | Range |
|---|---|---|
| Days to emergence | 3 weeks | 3-4 weeks |
| Days to flowering from date of planting tubers | 47 days | 40-52 |
| Days to maturity | 132 days | 128-135 days |
| Plant height (cm) | 82.3 cm | 79.7-92.5 cm |
| Length of lateral branches (cm) | 70.1 cm | 64-74.5 cm |
| Number of lateral branches | 6.8 | 5-8 |
| Spike/flower color | white | white |
| Leaf length (younger leaf taken from $5^{th}$ leaf from top of flowering stem) | 6.5 cm | 5.6-7.5 cm |
| Leaf length (older leaf taken from $5^{th}$ leaf from lower part of flowering stem) | 13 cm | 11-17.2 cm |
| Leaf width (younger leaf taken from $5^{th}$ leaf from top of flowering stem) | 3.4 cm | 3-4.8 cm |
| Leaf width (older leaf taken from $5^{th}$ leaf from lower part of flowering stem) | 11 cm | 9.5-13.2 cm |
| Leaf area ($cm^2$) of younger leaf taken from $5^{th}$ leaf from lower part of flowering stem | 30.54 $cm^2$ | 16.8-36.8 $cm^2$ |
| Leaf area ($cm^2$) of older leaf taken from $5^{th}$ leaf | 143 $cm^2$ | 104.5-227.4 $cm^2$ |

TABLE 4-continued

Phenotypic characteristics of KI969

| | Average | Range |
|---|---|---|
| from lower part of flowering stem | | |
| Tuber length | 8.58 ± 2.14 cm | 5.2 cm-14 cm |
| Tuber width | 6.14 ± 1.14 cm | 4.3 cm-8.7 cm |
| PI2 (mg/g) in dried tubers | 3.33 ± 0.66 mg/g | 2.51-4.63 |
| Average tuber yield/acre | 40,000 lbs/acre | 36,000-45,000 lbs/acre |
| Tuber characteristics | Slightly oblong, white skin, white flesh types | |

The present invention is related to the development of a novel, stable, clonal line of *Solanum tuberosum* L. KI964 is an F1 generated from the hybridization between two tetraploid S tuberosum lines. Both parental ines, Russent Nugget and KI-PSt0243 are heterozygous, resulting in a heterozygous F1 line designated KI969.

This clonal line is unique and clearly distinct from all other existing varieties of *Solamum tuberosum* L. Clonal line KI969 has robust agronomical characteristics, high tuber yield equivakent to commercial cultivars and produces tubers that have a consistently high P12 content. It is expected that if line KI969 is crossed with another compatible potato variety or line, at least some of the resulting plants will also have a high level of PI2.

*Solanum tuberosum* L. KI964 is an F1 generated from the hybridization between two tetraploid *S tuberosum* lines. Both parental lines, Russet Nugget and KI-PSt0243 are heterozygous, resulting in a heterozygous F1 line designated KI969.This clonal line is unique and clearly distinct from all other existing varieties of *Solanum tuberosum L*. Clonal line KI969 has robust agronomical characteristics, high tuber yield equivalent to commercial cultivars and produces tubers that have a consistently high PI2 content. It is expected that if line KI969 is crossed with another compatible potato variety or line, at least some of the resulting plants will also have a high level of PI2.

Various breeding schemes may be used to produce new potato clonal lines from KI969. In one method, generally referred to as the pedigree method, KI969 may be crossed with another different potato plant such as a second inbred parent potato plant, which either itself exhibits one or more selected desirable characteristic(s) or imparts selected desirable characteristic(s) to a hybrid combination. Examples of potentially desired characteristics include lower TGA, higher PI2, reduced time to crop maturity, better agronomic quality, resistance and/or tolerance to insecticides, herbicides, pests, heat and drought, and disease, stand establishment, growth rate, maturity and tuber size. If the two original parent potato plants do not provide all the desired characteristics, then other sources can be included in the breeding population. Elite lines can also be used as starting materials for breeding or source populations from which to develop novel lines.

Thereafter, resulting seed is harvested and resulting superior progeny plants are selected In yet another aspect of the invention, processes are provided for producing potato plants, which processes generally comprise crossing a first parent potato plant with a second parent potato plant wherein at least one of the first parent potato plant or the second parent potato plant is potato plant KI969. In some embodiments of the present invention, the first potato plant is KI969 and is a female and in other embodiments the first potato plant is KI969 and is a male. These processes may be further exemplified as processes for preparing hybrid potato seed or plants, wherein a first potato plant is crossed with a second potato plant of a different, distinct variety to provide a hybrid that has, as one of its parents, the inbred potato plant line KI969. In this case, a second potato line is selected which confers desirable characteristics when in hybrid combination with the first potato line.

Any time the potato plant KI969 is crossed with another, different potato, a first generation ($F_1$) potato hybrid plant is produced. As such, an $F_1$ hybrid potato plant may be produced by crossing KI969 with any second inbred potato plant. Therefore, any $F_1$ hybrid potato plant or potato seed which is produced with KI969 as a parent is part of the present invention.

For a decision to be made to advance a hybrid, it is not necessary that the hybrid be better than all other hybrids. Rather, significant improvements must be shown in at least some traits that would create value for some applications or markets. Some testcross hybrids are eliminated despite being similarly competitive relative to the current commercial hybrids because of the cost to bring a new hybrid to market requires a new product to be a significant improvement over the existing product offering.

All plants produced using potato plant KI969 as a parent are within the scope of this invention, including plants derived from potato plant KI969. This includes plants essentially derived from—KI969 with the term "essentially derived variety" having the meaning ascribed to such term in 7 U.S.C. § 2104(a)(3) of the Plant Variety Protection Act, which definition is hereby incorporated by reference. This also includes progeny plant and parts thereof with at least one ancestor that is potato plant KI969. All breeders of ordinary skill in the art maintain pedigree records of their breeding programs. These pedigree records contain a detailed description of the breeding process, including a listing of all parental lines used in the breeding process and information on how such line was used. Thus, a breeder would know if KI969 were used in the development of a progeny line, and would also know how many breeding crosses to a line other than KI969 were made in the development of any progeny line. A progeny line so developed may then be used in crosses with other, different, potato plants to produce potato hybrid plants with superior characteristics.

With the advent of molecular biological techniques that have allowed the isolation and characterization of genes that encode specific protein products, scientists in the field of plant biology developed a strong interest in engineering the genome of plants to contain and to express foreign genes, or additional, or modified versions of native or endogenous genes (perhaps driven by different promoters) to alter the traits of a plant in a specific manner. Such foreign, additional and/or modified genes are referred to herein collectively as "transgenes." The present invention, in particular embodiments, also relates to transformed versions of the claimed potato clonal line KI969 containing one or more transgenes, particularly genes that encode resistance to a herbicide.

Numerous methods for plant transformation have been developed, including biological and physical, plant transformation protocols. See, for example, Miki et al., "Procedures for Introducing Foreign DNA into Plants" in Methods in Plant Molecular Biology and Biotechnology, Glick, B. R. and Thompson, J. E. Eds. (CRC Press, Inc., Boca Raton, 1993) pages 67-88. In addition, expression vectors and in vitro culture methods for plant cell or tissue transformation and regeneration of plants are available. See, for example, Gruber et al., "Vectors for Plant Transformation" in Methods in Plant Molecular Biology and Biotechnology, Glick, B. R. and Thompson, J. E. Eds. (CRC Press, Inc., Boca Raton, 1993) pages 89-119.

The foregoing methods for transformation would typically be used for producing transgenic lines. Transgenic lines could then be crossed, with another (non-transformed or transformed) line, in order to produce a transgenic potato plant. Alternatively, a genetic trait which has been engineered into a particular potato line using the foregoing transformation techniques could be moved into another line using traditional crossing techniques that are well known in the plant breeding arts. For example, a crossing approach could be used to move an engineered trait from a public, non-elite line into an elite line, or from a hybrid potato plant containing a foreign gene in its genome into a line or lines which do not contain that gene.

In addition to phenotypic observations, a plant can also be described by its genotype. The genotype of a plant can be described through a genetic marker profile which can identify plants of the same variety, a related variety or be used to determine or to validate a pedigree. Genetic marker profiles can be obtained by techniques such as Restriction Fragment Length Polymorphisms (RFLPs), Randomly Amplified Polymorphic DNAs (RAPDs), Arbitrarily Primed Polymerase Chain Reaction (AP-PCR), DNA Amplification Fingerprinting (DAF), Sequence Characterized Amplified Regions (SCARs), Amplified Fragment Length Polymorphisms (AFLPs), Simple Sequence Repeats (SSRs) which are also referred to as Microsatellites, and Single Nucleotide Polymorphisms (SNPs), Isozyme Electrophoresis and Isolectric Focusing.

Particular markers used for these purposes are envisioned to include any type of genetically stable marker and marker profile which provides a means of distinguishing varieties.

Deposit Information

Applicant has made a deposit of at least 25 vials of nodes, with 8 to 12 viable nodes per vial, of potato line KI969 with the American Type Culture Collection (ATCC), 10801 University Boulevard, Manassas, Va. 20110-2209, USA, with ATCC Deposit No. PTA-123537, from which plants of potato line KI969 can be reproduced. The nodes were deposited with the ATCC on Oct. 20, 2016, and were obtained from the line maintained by Kemin Industries, Inc., 2100 Maury St, Des Moines, Iowa 50317, since prior to the filing date of this application. Access to these nodes will be available during the pendency of the application to the Commissioner of Patents and Trademarks and persons determined by the Commissioner to be entitled thereto upon request. Upon allowance of any claims in the application, the Applicant will make the deposit available to the public pursuant to 37 C.F.R. § 1.808. This deposit of potato line KI969 will be maintained in the ATCC depository, which is a public depository, for a period of 30 years, or 5 years after the most recent request, or for the enforceable life of the patent, whichever is longer, and will be replaced if it becomes nonviable during that period. Additionally, Applicant has or will satisfy all of the requirements of 37 C.F.R. §§ 1.801-1.809, including providing an indication of the viability of the sample upon deposit. Applicant has no authority to waive any restrictions imposed by law on the transfer of biological material or its transportation in commerce. Applicant does not waive any infringement of rights granted under this patent or under the Plant Variety Protection Act (7 USC 2321 et seq.).

The foregoing invention has been described in detail by way of illustration and example for purposes of clarity and understanding. As is readily apparent to one skilled in the art, the foregoing are only some of the methods and compositions that illustrate the embodiments of the foregoing invention. It will be apparent to those of ordinary skill in the art that variations, changes, modifications and alterations may be applied to the compositions and/or methods described herein without departing from the true spirit, concept and scope of the invention.

We claim:

1. A node of potato clonal line designated KI969, or a part thereof, representative nodes of the line having been deposited under ATCC Accession No. PTA-123537.

2. A plant grown from the nodes in claim 1.

3. A tuber grown from a plant grown from the node in claim 1.

4. A population of potato nodes comprising at least one potato node of claim 1.

5. A method for producing potato seed, said method comprising the steps of; (a) growing one or more plants from one or more of the the node of claim 1; (b) pollinating one or more plants produced from one or more of the node of claim 1 by self-pollination or by pollination with pollen from a different plant produced from the node of claim 1; and, (c) harvesting resultant seed.

6. A potato seed produced by the method of claim 5.

7. A part of the potato plant of claim 2, selected from the group consisting of an intact plant cell, a plant protoplast, pollen, an ovule, a tuber, a flower, a seed, a flower, a petal and a leaf.

8. Pollen of the plant of claim 2.

9. An ovule of the plant of claim 2.

10. A potato plant, or a part thereof, having all the physiological and morphological characteristics of the plant of claim 2, or a part thereof.

11. A population of plants comprising at least one plant of claim 2.

12. A method for producing a potato plant, said method comprising the step of: (a) crossing potato plant KI969, representative nodes of the line having been deposited under ATCC Accession No. PTA -123537, with another different potato plant to yield progeny potato seed.

13. The method of claim 12, wherein the other, different potato plant is an inbred potato plant.

14. The method of claim 12, further comprising the step of selecting plants obtained from growing at least one generation of the progeny potato seed for a desirable trait.

15. A method of introducing a desired trait from potato line KI969said method comprising the steps of: (a) crossing KI969 plants with plants of another potato line to produce F1 progeny plants; and (b) selecting F1 progeny plants that have the desired trait from potato line KI969.

* * * * *